Figure 1A:
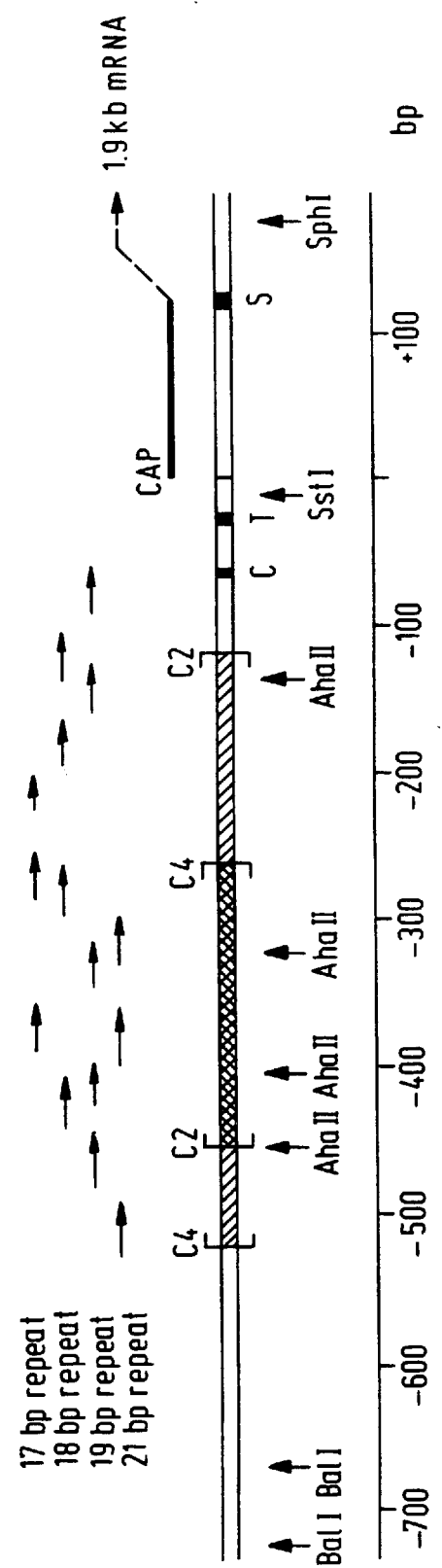

United States Patent [19]

Fleckenstein et al.

[11] Patent Number: 5,849,522
[45] Date of Patent: Dec. 15, 1998

[54] ENHANCER FOR EUKARYOTIC EXPRESSION SYSTEMS

[75] Inventors: Bernhard Fleckenstein, Schlaifhausen, Germany; Walter Schaffner, Weiningen, Switzerland; Frank Weber, Rheinfelden, Switzerland; Karoline Dorsch-Häsler, Zürich, Switzerland; Gerhard Jahn, Neunkirchen; Michael Boshart, Heidelberg, both of Germany

[73] Assignee: Hoechst Aktiengesellschaft, Frankfurt am Main, Germany

[21] Appl. No.: 467,143

[22] Filed: Jun. 6, 1995

Related U.S. Application Data

[63] Continuation of Ser. No. 37,658, Mar. 19, 1993, which is a continuation of Ser. No. 806,301, Dec. 19, 1991, abandoned, which is a continuation of Ser. No. 285,330, Dec. 14, 1988, abandoned, which is a continuation of Ser. No. 170,140, Mar. 14, 1988, abandoned, which is a continuation of Ser. No. 59,228, Jun. 4, 1987, abandoned, which is a continuation of Ser. No. 768,816, Aug. 23, 1985, abandoned.

[30] Foreign Application Priority Data

Aug. 24, 1984 [DE] Germany ............................ 34 31 140.8

[51] Int. Cl.$^6$ ............................ C12P 21/02; C07H 21/04; C12N 15/11; C12N 15/67
[52] U.S. Cl. ....................... 435/69.1; 435/172.3; 536/24.1
[58] Field of Search ................................ 435/69.1, 172.3; 536/24.1

[56] References Cited

U.S. PATENT DOCUMENTS 5,168,062  12/1992  Stinski ................................. 435/240.2

OTHER PUBLICATIONS

Greenaway et al., "Human cytomegalovirus DNA: BamHI, EcoRI and PstI restriction endonuclease cleavage maps," Gene, 18:355–360 (1982).

Stinski et al., "Organization and Expression of the Immediate Early Genes of Human Cytomegalovirus,"J. Virol., 46:1–14 (Apr. 1983).

Stenberg et al., "Structural Analysis of the Major Immediate Early Gene of Human Cytomegalovirus," J. Virol., 49:190–199 (Jan. 1984).

Clanton et al., "Neoplastic transformation by a cloned human cytomegalovirus DNA fragment uniquely homoloqous to one of the transforming regions of herpes simplex virus type 2," PNAS–USA, 80:3826–3830 (1983).

Nelson et al., "Structure of the Transforming Region of Human Cytomegalovirus AD169,"J. Virol., 49:109–115 (Jan. 1984).

Gorman et al., "Recombinant Genomes Which Express Chloramphenicol Acetyl–transferase in Mammalian Cells," Mol. Cell. Biol., 2:1044–1051 (1982).

Laimins et al., "Host–specific activation of transcription by tandem repeats from simian virus 40 and Moloney murine sarcoma virus," PNAS–USA, 79:6453–6457 (1982).

Kaufman et al., "Construction of a Modular Dihydrofolate Reductase cDNA Gene: Analysis of Signals Utilized for Efficient Expression," Mol. Cell. Biol., 2:1304–1319 (1982).

Dynan et al., "Isolation of Transcription Factors that Discriminate between Different Promoters Recognized by RNA Polymerase II," Cell, 32:669–680 (1983).

Breathnach et al., "Plasmids for the cloning and expression of full–length double–stranded cDNAs under control of the SV40 early or late gene promoter," Nucl. Acids Res., 11:7119–7136 (1983).

Kaufman et al., "Growth–Dependent Expression of Dihydrofolate Reductase mRNA from Modular cDNA Genes," Mol. Cell. Biol., 3:1598–1608 (1983).

Jahn et al., Journal of Virology, 49:363–370 (1984).

Weber et al.. Cell, 36:983–992 (1984).

Thomsen et al., Proc. Natl. Acad. Sci., 81:659–663 (1984).

Banerji et al., Cell 33:729–740 (1983).

Gillies et al., Cell, 33:717–728 (1983).

Okazaki et al., EMBO J., 4:2589–2595 (1985).

Theisen et al., EMBO J., 5:719–724 (1986).

Garabedian et al., Cell, 45:859–867 (1986).

Ciliberto et al., Cell, 41:531–540 (1985).

Edlund et al., Science, 230:912–916 (1985).

Boulet et al., Proc. Natl. Acad. Sci. (USA), 83:3599–3603 (1986).

*Primary Examiner*—Nancy Degen
*Attorney, Agent, or Firm*—Finnegan, Henderson, Farabow, Garrett & Dunner, L.L.P.

[57] ABSTRACT

An enhancer has been located in the upstream region of the major immediate early gene of human cytomegalovirus and has been isolated, which enhancer is more active than that from SV40 and has a wide host cell spectrum. Hence, it is suitable for eukaryotic expression systems wherein it can be incorporated upstream or downstream of the structural gene or of the regulation region.

4 Claims, 2 Drawing Sheets

FIG. 1b

```
-737 AATCAATATT GGCCATAGC CATATTATTC ATTGGTTATA TAGCATAAAT CAATATTGGC TATTGGCCAT TGCATACGTT GTATCCATAT CATAATATGT
          Bal I
-637 ACATTATAT TGGCTCATGT CCAACATTAC CGCCATGTTG ACATTGATTA TTGACTAGTT ATTAATAGTA ATCAATTACG GGTCATTAG TTCATAGCCC
-537 ATATATGGAG TTCCGGGTTA CATAACTTAC GGTAAAATGG CCGGCCTGTCT GACCGCCCAA CGACCCCCGC CCATTGACGT CAATAATGAC GTATGTTCCC
              C4                               C4
-437 ATAGTAACGC CAATAGGGAC TTTCCATTGA CGTCAATGGG GCCCGCCCTG GCATTATGCC ACGGTAAACT GCCCACTTGG CAGTACATCA AGTGTATCAT ATGCCAAGTA
                                                                                                             C4
-337 CGCCCCCTAT TGACGTCAAT GACGGTAAAT GGCCCGCCTG GCATTATGCC CAGTACATGA CCTTATGGGA GTTTGACTCA CGGGGATTTC CAAGTCTCCA CCCCATTGAC
                                                                                                          C2
-237 AGTCATCGCT ATTACCATGG TGATGCGGTT TTGGCAGTAC ATCAATGGGC GTGGATAGCG GTTTGACTCA CGGGGATTTC CAAGTCTCCA CCCCATTGAC
-137 GTCAATGGGA GTTTGTTTTG GCACCAAAAT CAACGGGACT TTCCAAAATG TCGTAACAAC TCCGCCCCAT TGACGCAAAT GGGCGGTAGG CGTGTACGGT
                                                                                      C4
-37 GGGAGGTCTA TATAAGCAGA GCTGGTTTAG TGAACCGTCA GATCGCCTGG AGACGCCATC CACGCTGTTT TGACCTCCAT AGAAGACACC GGGACCGATC
                Sst I                         +1
+64 CAGCCTCGGC GGCCGGGAAC GGTGCATTGG AAGCGGGATT CCCCGTGCCA AGAGTGACGT AAGTACCGCC TATAGAGTCT ATAGGCCCAC CCCCTTGGCT
+164 TCTTATGCAT GCTATACTGT TTTTGGCTTG
          Sph I
```

1

ENHANCER FOR EUKARYOTIC EXPRESSION SYSTEMS

This is a continuation of application Ser. No. 08/037,658, filed Mar. 19, 1993, which is a continuation of application Ser. No. 07/806,301, filed Dec. 13, 1991, now abandoned, which is a continuation of application Ser. No. 07/285,330, filed Dec. 14, 1988, now abandoned, which is a continuation of application Ser. No. 07/170,140, filed Mar. 14, 1988, now abandoned, which is a continuation of application Ser. No. 07/059,228, filed Jun. 4, 1987, now abandoned, which is a continuation of application Ser. No. 06/768,816, filed Aug. 23, 1985, now abandoned.

The invention is directed to an enhancer for eukaryotic expression systems, containing DNA from the upstream region of the major immediate early (IE) region of human cytomegalovirus (HCMV). According to certain embodiments, the enhancer is obtainable by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA, and enhancer-active mutants of this DNA. A process for improvement of eukaryotic expression systems by incorporating the enhancer upstream or downstream of the structural gene or of the regulation region is also provided. According to certain embodiments, the enhancer is incorporated not more than about 7,000 bp, or about 3,000 bp, upstream or downstream of the sites specified.

The "enhancer trap" is described in F. Weber et al., Cell 36 (1984) 983–992; in respect of HCMV DNA, see G. Jahn et al., J. Virology, February 1984, Vol. 49, 363–370 and Literature quoted there, also D. R. Thomsen et al., Proc. Natl. Acad. Sci. USA, 81 (1984), 659–663, and P. J. Greenaway et al., Gene 18 (1982) 355–360.

In the HCMV DNA, the enhancer is located in the Hind III E fragment (Greenaway et al., loc. cit.), which includes the Pst I m fragment (about 2.1 kb).

Two recombinants were isolated by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA, and enhancer-active mutants of this DNA. Those recombinants contained 341 and 262 bp of HCMV DNA, located at positions –118 to –458 and –263 to –524 respectively on the published DNA sequence (Greenaway et al., loc. cit.). The overlap of 196 bp contains an essential part of the enhancer. Deletion mutants, for example obtained by Aha II and religation of the fragments in various combinations, are likewise enhancer-active.

The invention also relates to DNA which is a sequence homolog of reisolated HCMV specific enhancer DNA to the extent of at least 75, preferably at least 80, %, or is hybridized therewith.

The enhancer increases the expression of rabbit beta-globin in HeLa cells, after incorporation downstream of the appropriate gene, by at least two orders of magnitude, irrespective of the orientation. Thus the enhancer is superior to that of SV40 by the factor 3 to 5, dependent on the host system.

The HCMV enhancer has activity in a broad spectrum of host cells (cells of primates, mice, rats and frogs). It stimulates the expression of proteins in eukaryotic systems and thus facilitates the production of modified proteins, for example glycoproteins.

It is also possible to eliminate the promoter instrinsic to HCMV, for example by deletion of about 100 bp using Bal 31 beyond the Sac I restriction site. Where appropriate, the enhancer sequence can be modified by the attachment of adaptors or linkers.

When used with the intrinsic promoter, it is possible for a eukaryotic promoter to be substituted, for example by incorporation with inclusion of the first splice donor consensus sequence of the IE gene before the splice acceptor sequence of the gene which is to be expressed.

The invention is illustrated in detail in the Example which follows.

EXAMPLE

An "enhancer trap" was prepared, by the method of Weber et al., loc. cit., by removal of the 72 bp repeat region (restriction with XbaI and KpnI) from the SV40 genome. The PstI m fragment (2.1 kb) from HCMV, strain AD 169, was broken down by sonication into fragments about 300 bp in size, and co-transfection with the "enhancer trap" was carried out. The recombinant DNA was isolated from the colonies which showed the best lytic growth. By sequencing, a 262 bp segment of HCMV DNA was found in which an end-on-end ligation had occurred on one side, whereas on the other side recombination took place via a 6 bp homology between HCMV (nucleotides –531 to –526, FIG. 1a) and SV40 (nucleotides 67 to 72). This resulted in a deletion of 27 bp of the SV40 DNA (nucleotides 73 to 99), which affected both 21 bp repeats of the SV40 early promoter. The 262 bp segment is identified in the restriction map (FIG. 1a) and in the DNA sequence (FIG. 1b) by square brackets labeled "C4".

Another enhancer-active recombinant with 341 bp of HCMV DNA proved to be a ligation product having the ends of a linear "enhancer trap" molecule (in which a few bases had been eliminated from the KpnI and XbaI ends of the SV40 DNA, presumably by exonucleolytic deletion before ligation within the transfected cell). The HCMV DNA of this recombinant is identified in FIGS. 1a and 1b by "C2"; it extends from –188 to –458. Thus the segments C2 and C4 overlap over a region of 196 bp.

The Hind III C fragment of the recombinant virus with the C4 insert, and the PstI m fragment of HCMV were first cloned in pUC 8 (J. Vieira et al., Gene 19 (1982) 259–268) in both orientations, excized as Hind III-SalI fragments, and recloned between the HindIII and XhoI restriction site of pβX14, that is to say downstream of the rabbit β-globin gene (J. Banerji et al., Cell 27 (1981) 299–308; J. de Villiers et al., Nucl. Acids Res. 9 (1981) 6251–6254; S. Rusconi et al., Proc. Natl., Acad. Sci. USA 78 (1981) 5051–5055; H. Weber et al., ICN-UCLA Symp. Mol. Cell. Biol. 33 (1981) 367; B. Wasylyk et al., Cell 32 (1983) 503–514). The enhancer action on β-globin transcription was determined by S1 nuclease analysis of cytoplasmic RNA after transient expression in HeLa cells.

All recombinants were compared under standardized conditions with analogous recombinants having the SV40 enhancer. It emerged that the HCMV enhancer increases the synthesis of β-globin by at least 2 orders of magnitude—irrespective of the orientation.

We claim:

1. The method to increase expression of a gene in a mammalian cell comprising inserting into a mammalian cell an isolated DNA enhancer consisting of DNA from the upstream region of the major immediate early (IE) gene of human cytomegalovirus (HCMV) and a heterologous gene that is to be expressed, wherein the DNA from the upstream region of the IE gene of HCMV is the only HCMV material to which the mammalian cell is exposed.

2. The method as claimed in claim 1, wherein the DNA enhancer consists of the DNA from the PstI restriction enzyme site upstream of the transcription start site to position –118 of the PstI-m fragment, or an enhancer-active part thereof.

3. The method as claimed in claim 1, wherein the DNA enhancer is included approximately 7000 base pairs upstream or downstream of the heterologous gene.

4. The method as claimed in claim 1, wherein the DNA enhancer is included approximately 3000 base pairs upstream or downstream of the heterologous gene.

* * * * *

UNITED STATES PATENT AND TRADEMARK OFFICE
CERTIFICATE OF CORRECTION

PATENT NO. : 5,849,522
DATED : December 15, 1998
INVENTOR(S) : Bernhard FLECKENSTEIN et al.

It is certified that error appears in the above-indentified patent and that said Letters Patent is hereby corrected as shown below:

Claim 1, column 2, line 63, "The Method" should read
--A Method--.

Signed and Sealed this

Twenty-eighth Day of December, 1999

Attest:

Q. TODD DICKINSON

Attesting Officer

Acting Commissioner of Patents and Trademarks